(12) United States Patent
Bateman et al.

(10) Patent No.: US 11,564,694 B2
(45) Date of Patent: Jan. 31, 2023

(54) SMART TOURNIQUET

(71) Applicant: TAKEDA PHARMACEUTICAL COMPANY LIMITED, Osaka (JP)

(72) Inventors: Danielle Bateman, Singapore (SG); Qi-Dong Dai, Shanghai (CN); Qing Gu, Shanghai (CN); Seok-Choon Toh, Singapore (SG)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 858 days.

(21) Appl. No.: 16/476,737

(22) PCT Filed: Jan. 11, 2018

(86) PCT No.: PCT/US2018/013330
§ 371 (c)(1),
(2) Date: Jul. 9, 2019

(87) PCT Pub. No.: WO2018/132577
PCT Pub. Date: Jul. 19, 2018

(65) Prior Publication Data
US 2019/0350593 A1 Nov. 21, 2019

Related U.S. Application Data

(60) Provisional application No. 62/445,643, filed on Jan. 12, 2017.

(51) Int. Cl.
*A61B 17/00* (2006.01)
*A61B 17/132* (2006.01)
(Continued)

(52) U.S. Cl.
CPC .......... *A61B 17/1322* (2013.01); *A61B 34/25* (2016.02); *A61M 5/31568* (2013.01);
(Continued)

(58) Field of Classification Search
CPC ............ A61B 17/1322; A61B 17/1327; A61B 2017/00026; A61B 2017/00115;
(Continued)

(56) References Cited

U.S. PATENT DOCUMENTS

| 4,321,929 A | 3/1982 | Lemelson et al. |
| 5,314,437 A | 5/1994 | Holtsch |

(Continued)

FOREIGN PATENT DOCUMENTS

| EP | 2 789 355 A1 | 10/2014 |
| WO | 2016/087123 A1 | 6/2016 |
| WO | 2017/172756 A1 | 3/2017 |

OTHER PUBLICATIONS

Notice of Reasons for Rejection issued with corresponding Japanese Patent Application No. 2019-537356 dated Oct. 12, 2021 (including English Translation).

(Continued)

*Primary Examiner* — George Manuel
(74) *Attorney, Agent, or Firm* — Troutman Pepper Hamilton Sanders LLP

(57) ABSTRACT

A smart tourniquet for self-administering a medication is provided. When a patient needs to inject themselves with a medication, intravenously, called an "infusion," the patient wears the smart tourniquet around their arm and tightens the device. While the patient is using the smart tourniquet, the device automatically records the date and time of the infusion, called a "timestamp". The patient can also use the device to record the dosage or "number of units" taken at the time of the infusion. The smart tourniquet can store the timestamp as well as other related information as a record. At a later time, the patient can recall prior records on the smart tourniquet itself. The smart tourniquet can also be synchronized with an application and the records can be (Continued)

downloaded for review by the patient, nurse or doctor to render accurate and timely care.

19 Claims, 15 Drawing Sheets

(51) Int. Cl.
*A61B 34/00* (2016.01)
*A61M 5/315* (2006.01)
*A61M 5/42* (2006.01)

(52) U.S. Cl.
CPC ... *A61M 5/425* (2013.01); *A61B 2017/00026* (2013.01); *A61B 2017/00199* (2013.01); *A61B 2017/00221* (2013.01); *A61M 2205/52* (2013.01)

(58) Field of Classification Search
CPC .......... A61B 2017/00199; A61B 2017/00221; A61B 2090/0803; A61B 34/25; A61M 2205/52; A61M 5/31568; A61M 5/425; G16H 20/17; G16H 40/63
See application file for complete search history.

(56) References Cited

U.S. PATENT DOCUMENTS

| | | | |
|---|---|---|---|
| 5,911,735 A | 6/1999 | McEwen et al. | |
| 6,682,547 B2 | 1/2004 | McEwen et al. | |
| 7,955,352 B2 | 6/2011 | McEwen et al. | |
| 8,043,327 B1 | 10/2011 | Arias et al. | |
| 9,814,467 B2 | 11/2017 | McEwen et al. | |
| 2004/0224879 A1* | 11/2004 | Wolff | A61K 48/0075 514/8.1 |
| 2005/0240109 A1* | 10/2005 | Inoue | A61B 5/021 600/490 |
| 2006/0200195 A1 | 9/2006 | Yang | |
| 2007/0032819 A1 | 2/2007 | McEwen et al. | |
| 2008/0058664 A1 | 3/2008 | Mirro | |
| 2008/0167572 A1 | 7/2008 | Stivoric et al. | |
| 2008/0177159 A1 | 7/2008 | Gavriely | |
| 2008/0262535 A1 | 10/2008 | Gavriely et al. | |
| 2009/0216132 A1 | 8/2009 | Orbach | |
| 2010/0234877 A1 | 9/2010 | Pienkowski et al. | |
| 2011/0004276 A1* | 1/2011 | Blair | A61B 5/0006 607/60 |
| 2013/0345610 A1 | 12/2013 | Larson et al. | |
| 2015/0313608 A1 | 11/2015 | Baudenbacher et al. | |
| 2017/0325825 A1 | 11/2017 | Bybordi | |

OTHER PUBLICATIONS

Extended European Search Report issued in corresponding European Patent Application No. 18 73 9230 dated Sep. 24, 2020.

Office Action issued with corresponding Chinese Patent Application No. 201880010413.4 dated Jan. 6, 2022 (including English Translation).

* cited by examiner

Operation: Wake up the smart tourniquet by: a) fastening the smart tourniquet around patient's arm in preparation for infusion or b) press the function button on the smart tourniquet for 3 seconds (or other amount of time).

Display: 

Record: Insert first record (SN = 1) into the database

| SN | Time | Strength | Dosage |
|---|---|---|---|
| 1 | 2017.01.01 21:30 | NULL | NULL |

Operation: Press '+' or '-'button on the smart tourniquet to switch to the 'Dosage' screen.

Display: 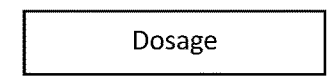

Record: N/A

Operation: Press function button on the smart tourniquet to confirm last saved strength and dosage.

Display: 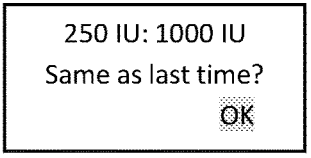

Record: Insert second record (SN=2) into the database.

| SN | Time | Spec | Dosage |
|---|---|---|---|
| 1 | 2017.01.01 21:30 | NULL | NULL |
| 2 | 2017.01.01 21:33 | 250 IU | 1000 IU |

FIG. 9B

Operation: Press '+' '-'button on the smart tourniquet to choose the strength. Press function button on the smart tourniquet to show the screen for inputting the dosage.

Display: 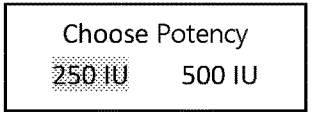

Record: NA

FIG. 10A

Operation: Press '+' '-' button on the smart tourniquet to increment/decrement the dosage by the strength.

Display: 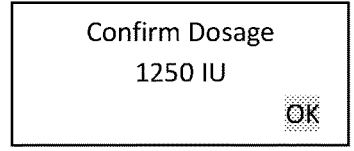

Record: NA

FIG. 10B

Operation: Press function button on the smart tourniquet to confirm the strength and dosage.

Display: 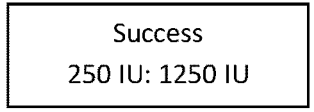

Record: Insert third record (SN=3) into the database.

| SN | Time | Spec | Dosage |
|---|---|---|---|
| 1 | 2017.01.01 21:30 | NULL | NULL |
| 2 | 2017.01.01 21:33 | 250 IU | 1000 IU |
| 3 | 2017.01.01 21:35 | 250 IU | 1250 IU |

FIG. 10C

Operation: Press '+' '-'button on the smart tourniquet to switch to the 'Records' screen Display: 

Record: NA

FIG. 11A

Operation: Press function button on the smart tourniquet to show the screen for querying saved records.

Display: 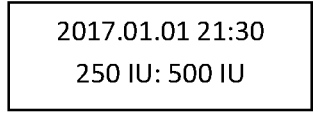

Record: NA

FIG. 11B

Operation: Press '-' button on the smart tourniquet to display previous records and press '+' button to display next records.

Display: 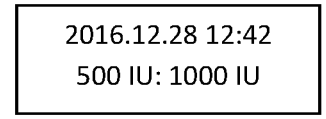

Record: NA

FIG. 11C

Operation: Press function button on the smart tourniquet to return to the 'Records' screen.

Display: 

Record: NA

FIG. 11D

Operation: Press '+' '-'button on the smart tourniquet to switch to the 'Time Adjustment' screen.

Display: 

Record: NA

Operation: Press function button on the smart tourniquet to enter the time adjustment function.

Display: 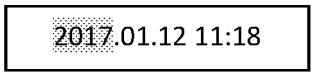

Record: NA

Operation: With each press of the function button on the smart tourniquet, a number flashes from left to right, one by one. Press '+' '-'button on the smart tourniquet to increase or decrease the number.

Display: 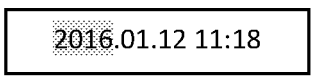

Record: NA

FIG. 12C

Operation: When the last number flashes, press function button on the smart tourniquet again to return to the 'Time Adjustment' screen.

Display: 

Record: adjusted time

Operation: Press '+' '-'button on the smart tourniquet to switch to the 'Language' screen.

Display: 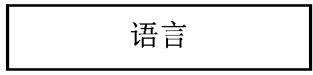

Record: NA

Operation: Press function button on the smart tourniquet to show the screen for selecting the language.

Display: 

Record: NA

FIG. 13B

Operation: Press '+' '-'button on the smart tourniquet to switch language and highlight the selected language.

Display: 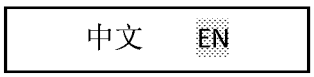

Record: NA

Operation: Press function button on the smart tourniquet and return to the 'Language' screen.

Display: 

Record: NA

Operation: The patient is asked to confirm a connection between the smart tourniquet and an application in response to the application requesting that the connection be established. Press function button on the smart tourniquet to confirm the connection, or hold '+' button to cancel.

Display: 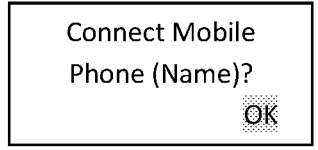

FIG. 14

SMART TOURNIQUET

FIELD OF THE INVENTION

The invention generally relates to a device and in particular to a smart tourniquet for recording, automatically, a date and time of when medication is self-administered by a patient.

BACKGROUND

Hemophilia is a medical condition in which the ability of blood to clot is severely reduced, causing a sufferer to bleed severely from even a slight injury. Deep internal bleeding, especially in the knees, ankles and elbows, can damage organs and tissues, and may be life-threatening. Hemophilia A or "classical hemophilia," is the most common form of hemophilia (1 in 4,000 to 1 in 5,000 males worldwide are born with this disorder). Patients with hemophilia A are prone to frequent hemorrhages as a result of a lack of Factor VIII. This congenital deficiency has been successfully treated by infusions of Factor VIII concentrate preparations isolated and purified from either blood plasma of donors having normal levels of Factor VIII, or from cell cultures genetically engineered to express the Factor VIII coagulant protein.

SUMMARY

While there is no cure for hemophilia, most hemophilia sufferers can and do lead fairly normal lives by taking infusions of recombinant Factor VIII whenever they bleed (e.g., because of an injury or surgery). Some people strive for "zero days of bleeding" by taking prophylactic infusions, for example, every two days or every three days. In either case, there is a need to track the date and time of a bleed and/or infusion. A hemophilia sufferer can use an application (e.g., one running on their smart phone) to record their bleeding episodes and/or infusions. Every time the person bleeds and/or takes an infusion, they can enter the date and time into the application.

Sometimes, however, a hemophilia sufferer is in a lot of pain when they are bleeding and taking an infusion to stop the bleeding. The pain makes it very difficult for the person to record the date and time of the bleed and/or infusion. Often a hemophilia sufferer is more interested in carrying on with what they were doing before an infusion and they sometimes forgets to record the date and time of their bleed and/or infusion. Incomplete information about bleeds and/or infusions or a delay in delivering this information to a health care provider can lead to misjudging the person's condition or missing a time or window for treating the person. The end result can be pain and suffering or much worse. What is needed is a way from a hemophilia sufferer to record the date and time of a bleed and/or infusion, automatically, with as little intervention as possible.

Accordingly, a smart tourniquet is provided that records, automatically, the date and time of a bleed and/or infusion, each time a patient uses the smart tourniquet for an infusion. Examples of the smart tourniquet include an elongate member having a first end and a second end. There is a longitudinal axis extending between the first end and the second end. The elongate member is adapted for wrapping about a limb of a patient, such as their arm. The smart tourniquet further includes a recording module. The recording module has a slot extending through it for slidably receiving the elongate member and a fastening end for releasably capturing the second end of the elongate member. When the elongate member is wrapped about the patient's limb and the second end of elongate member is captured by the fastening end and fixed to the recording module, pulling the first end of the elongate member away from the second end in the longitudinal direction tightens the smart tourniquet about the limb. This action also causes the recording module to save a record, including a timestamp of the patient using the tourniquet to self-administer the infusion.

The recording module can save a confirmation timestamp in response to the patient confirming a strength and dosage of the drug. The recording module can include a display and one or more keys for: i) entering the dosage of the drug self-administered by the patient so that the record includes the timestamp and the dosage, ii) inquiring about past records, iii) adjusting the timestamp, iv) changing the language of text displayed by the recording module or v) a combination thereof. The recording module can include a function key, which when depressed and held for at least a pre-defined period of time causes the recording module to save the timestamp of the patient using the tourniquet to self-administer the drug. The recording module can include memory for storing the record and previous records with earlier timestamps of the patient using the tourniquet to self-administer the drug.

The recording module can also include a wireless interface for communicating with a computing device, for example, using BLUETOOTH, WIFI, ZIGBEE or ZWAVE. The recording module can include an audio alarm configured to provide an aural cue in response to the fastening end of the recording module capturing the second end of the elongate member. The recording module can also include a visual alarm configured to provide a visual cue in response to the fastening end of the recording module capturing the second end of the elongate member.

In some examples of the smart tourniquet, the second end of the elongate member and fastening end of the recording module can form a buckle assembly comprising a male portion and a female portion. The recording module can shut off in response to the second end being released from the fastening end.

One example of the smart tourniquet includes an electrode electrically coupled to the recording module for measuring a galvanic skin response. When the smart tourniquet is tightened about the patient's limb, the electrode contacts the patient's skin. The recording module then saves the timestamp in response to the galvanic skin response measured by the electrode.

An associated method for tracking when a patient self-administers a drug includes providing a smart tourniquet. The smart tourniquet includes an elongate member having a first end and a second end. There is a longitudinal axis extending between the first end and the second end. The elongate member is adapted for wrapping about a limb of a patient, such as their arm. The smart tourniquet further includes a recording module. The recording module has a slot extending through it for slidably receiving the elongate member and a fastening end for releasably capturing the second end of the elongate member. When the elongate member is wrapped about the patient's limb and the second end of elongate member is captured by the fastening end and fixed to the recording module, pulling the first end of the elongate member away from the second end in the longitudinal direction tightens the smart tourniquet about the limb. This action also causes the recording module to save a record, including a timestamp of the patient using the tourniquet to self-administer the infusion.

The method further includes saving in the recording module a record that includes a timestamp of the patient using the tourniquet to self-administer a drug. Saving the record is in response to the second end of elongate member being captured by the fastening end of the recording module and the tourniquet being tighten about the limb.

Advantageously, using the smart tourniquet can help the patient record when they took an infusion of a drug. Moreover, the usefulness of the smart tourniquet is not tied to particular drug but can be extended to include any drug administered, intravenously, made by any pharmaceutical company. As such, the smart tourniquet can be widely adopted by pharmaceutical companies and patients alike.

BRIEF DESCRIPTION OF THE DRAWINGS

FIGS. 8, 9A-B, and 10A-C are diagrams showing a patient using the smart tourniquet to take an infusion, including waking up the smart tourniquet and inputting the dosage taken.

FIGS. 11A-D are diagrams showing a patient using the smart tourniquet to review infusion records stored in the device.

FIGS. 12A-D are diagrams showing a patient adjusting the time on the smart tourniquet.

FIGS. 13A-D are diagrams showing a patient selecting which language the smart tourniquet communicates with the patient.

FIG. 14 is a diagram showing the patient confirming that a connection between the smart tourniquet and the application be established.

DETAILED DESCRIPTION

Examples of a smart tourniquet for a patient to use to administer medication to themselves are described with reference to the figures. When the patient needs to inject themselves with medication, intravenously, called an "infusion," the patient wears the smart tourniquet around their arm, for example, and tightens the smart tourniquet. Tightening the smart tourniquet helps the patient locate a vein for the infusion. While the patient is using the smart tourniquet, the device can automatically record, the date and time of the infusion, called a "timestamp". The patient can also use the smart tourniquet to record the dosage or "number of units" of medication taken at the time of the infusion. The smart tourniquet can store the timestamp as well as other related information as a record. At a later time, the patient can recall prior records on the smart tourniquet itself. In another example, the smart tourniquet can be synchronized with an application and records can be downloaded from the smart tourniquet for review by the patient, nurse or doctor.

A hemophilia sufferer can use the smart tourniquet to take an infusion of recombinant Factor VIII, such as ADVATE produced by the SHIRE pharmaceutical company. They take the infusion whenever they bleed, which can occur spontaneously or as a result of an injury, to stop the bleeding. In this case, a timestamp of an infusion also represents a date and time of a bleeding episode. As such, any discussion below of the smart tourniquet recording a timestamp of an infusion also applies to recording a timestamp of a bleeding episode. Automatically recording the date and time when a hemophilia sufferer bleeds is particular beneficial because they may be in too much pain to record a bleeding episode themselves or they may forget.

Figure 1:
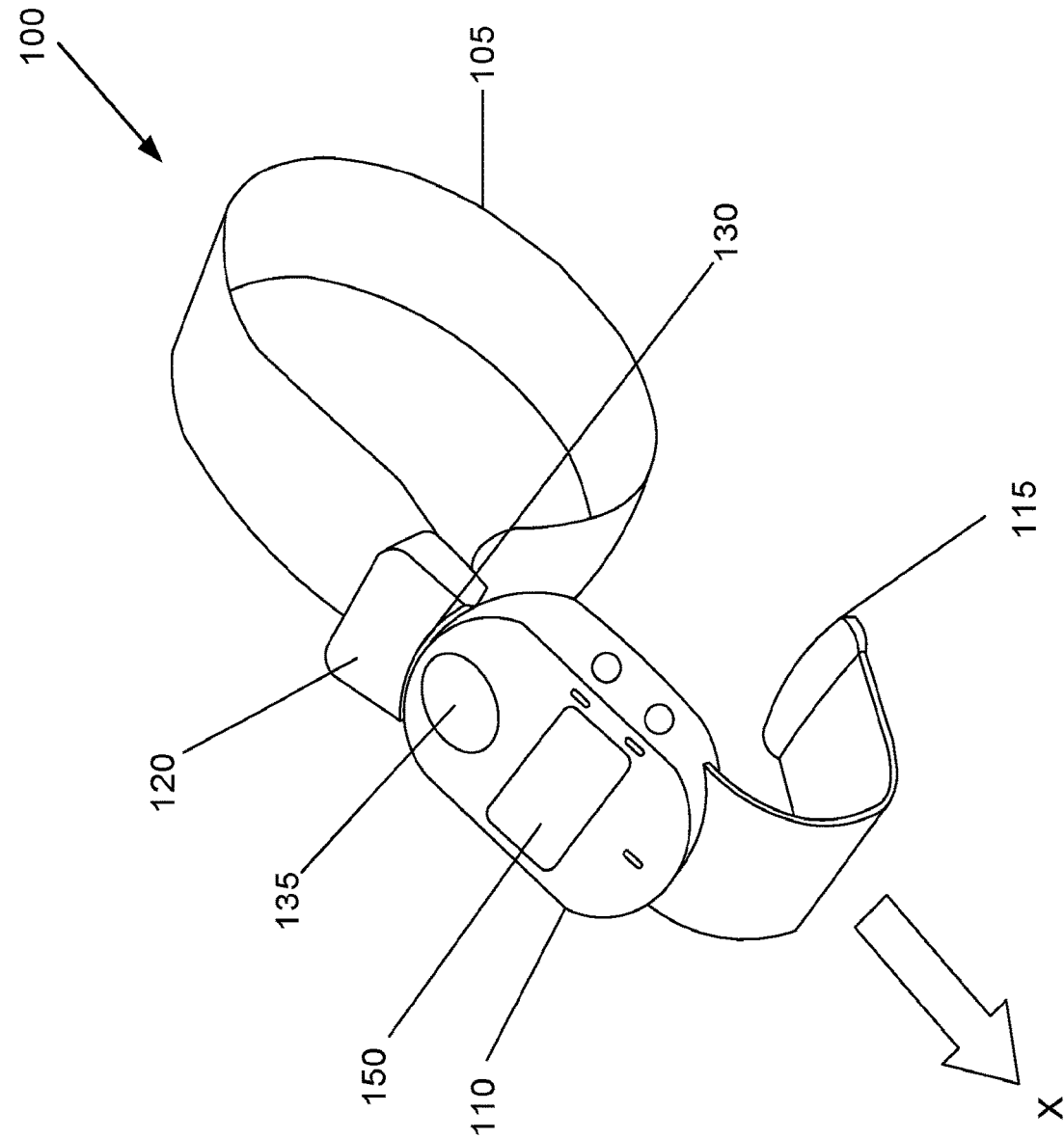
FIG. 1 is a perspective view of a smart tourniquet.

FIG. 1 shows an example of the smart tourniquet 100 having an elongate member 105 for wrapping tightly around a patient's limb during an infusion and a recording module 110 for recording a timestamp of the infusion (or bleeding episode). The elongate member 105 has a first end 115 and second end 120, and a longitudinal axis extending between the first and second ends 115, 120 (shown in FIG. 2 as a double-headed arrow labeled LA). The elongate member 105 is of a sufficient length of that allows the first end 115 to be pulled on while the second end 120 is wrapped around the patient's limb. The elongate member 105 can be of different lengths to accommodate different limb sizes, for example, a longer elongate member 105 for an adult arm and a shorter elongate member 105 for a child arm. The elongate member 105 can be made of a material that is compatible with the patient's skin, for example vinyl if the patient is allergic to latex.

The recording module 110 includes a slot 125 (shown in FIG. 2 in phantom line) through which the elongate member 105 can slide. As shown in FIG. 1, the long dimension of the recording module 110 is aligned with the longitudinal axis LA of the elongate member 105. The recording module 110 further includes, along its short dimension, a fastening end 130 that is adapted to releasably capture the second end 120 of the elongate member 105. To use the smart tourniquet 100, the patient wraps the second end 120 of the elongate number 105 around a limb, for example their arm, and fastens the second end 120 to the fastening end 130 of the recording module 110. This forms a loop about the second end 120 of the elongate member 105 around the patient's limb. The patient pulls the first end 115 of the elongate member 105 away from the second end 120 in the direction of the longitudinal axis (shown in FIG. 1 as arrow labeled X). This tightens the loop around the around the patient's limb and reduces blood circulation in the limb. The reduction in blood circulation causes veins near the surface of the patient's skin to enlarge and become more pronounced, thereby helping the patient locate a vein for the infusion. After the infusion, the patient can push a release button 135 on the recording module 110 to uncouple the second end 120 of the elongate number 105 from the fasting end 130 of the recording module 110.

In a convenient example of the smart tourniquet 100, the second end 120 of the elongate member 105 and the fastening end 130 of the recording module 110 can form a buckle. The second end 120 is the male portion of the buckle and the fastening end 130 is the female portion of the buckle. In using this example, fastening the smart tourniquet 100 includes inserting the second end 120 into the fastening end 130. In an alternative example, the gender of the second end 120 and the fastening end 130 are reversed, and the fastening end 130 is inserted into the second end 120 to fasten the smart tourniquet 100.

The smart tourniquet 100 can include mechanisms that help the patient use the device correctly. For example, the recording module 110 can include an audio alarm configured to provide an aural cue in response to the fastening end 130 of the recording module 110 capturing the second end 120 of the elongate member 105. By way of a non-limiting example, a single chirp from the audio alarm confirms that the smart tourniquet 100 is properly fastened around the patient's limb. In contrast, an absent of noise from the audio alarm, signifies that the smart tourniquet 100 is not properly fastened around the patient's limb.

In another example of the smart tourniquet 100, the recording module 110 can include a visual alarm configured to provide a visual cue in response to the fastening end 130 of the recording module 110 capturing the second end 120 of the elongate member 105. By way of a non-limiting example, a green light from the visual alarm confirms that the smart tourniquet 100 is properly fastened around the patient's limb. In contrast, a red light from the visual alarm signifies that the smart tourniquet 100 is not properly fastened around the patient's limb. In still yet another example of the smart tourniquet 100, a combination of aural and visual cues can be used to notify the patient whether they are using the device correctly. Advantageous, based on such aural and/or visual cues, the patient can readily know if they are using the smart tourniquet 100 correctly.

As described above, the smart tourniquet 100 can automatically document a timestamp of an infusion. In a convenient example, the smart tourniquet 100 records a timestamp when the device is fastened around the patient's arm, for example. In this way, a timestamp is recorded without the patient manually entering a date and time into the smart tourniquet 100. Fastening the smart tourniquet 100 around the patient's arm brings the smart tourniquet into contact with the patient's skin. One or more electrodes associated with the smart tourniquet 100 measure the conductance of the patient's skin, which is very different than air (as would be case if the smart tourniquet was not fastened around the patient's arm). Upon detecting the galvanic skin response, the smart tourniquet 100 records a timestamp. For ease of reference, this timestamp is called the "wakeup timestamp".

The smart tourniquet 100 also records the date and time when the patient confirms the strength and dosage of an infusion, which for ease of reference, is called the "confirmation timestamp." Again, a timestamp is recorded without the patient manually entering a date and time into the smart tourniquet 100. The wake up timestamp and the confirmation timestamp can be used to track when the user has taken an infusion and/or has had a bleeding episode, as will describe in greater detail below.

Additionally, records including the wakeup and confirmation timestamps can be used to identify when information about an infusion/bleeding episode is missing and to remind the patient to provide the missing information. For example, when a record of wakeup timestamp is not followed by a record of a confirmation timestamp, there may be information missing about an infusion/bleeding episode. The smart tourniquet 100 or an application associated with the device (an example of such application is described below with reference to FIG. 6) can prompt the patient to enter the missing date, time, strength, and dosage.

The process of reminding the patient to record infusion/bleeding episode information can also be based on time. For example, when the smart tourniquet 100 records a wakeup timestamp, a timer starts counting down. If the smart tourniquet 100 does not record a confirmation timestamp by the time the timer expires, the smart tourniquet 100 (or device) reminds the patient to provide information about an infusion/bleeding episode. Advantageously, the foregoing reduces the likelihood of information about an infusion or bleeding episode not being recorded.

Figure 2:
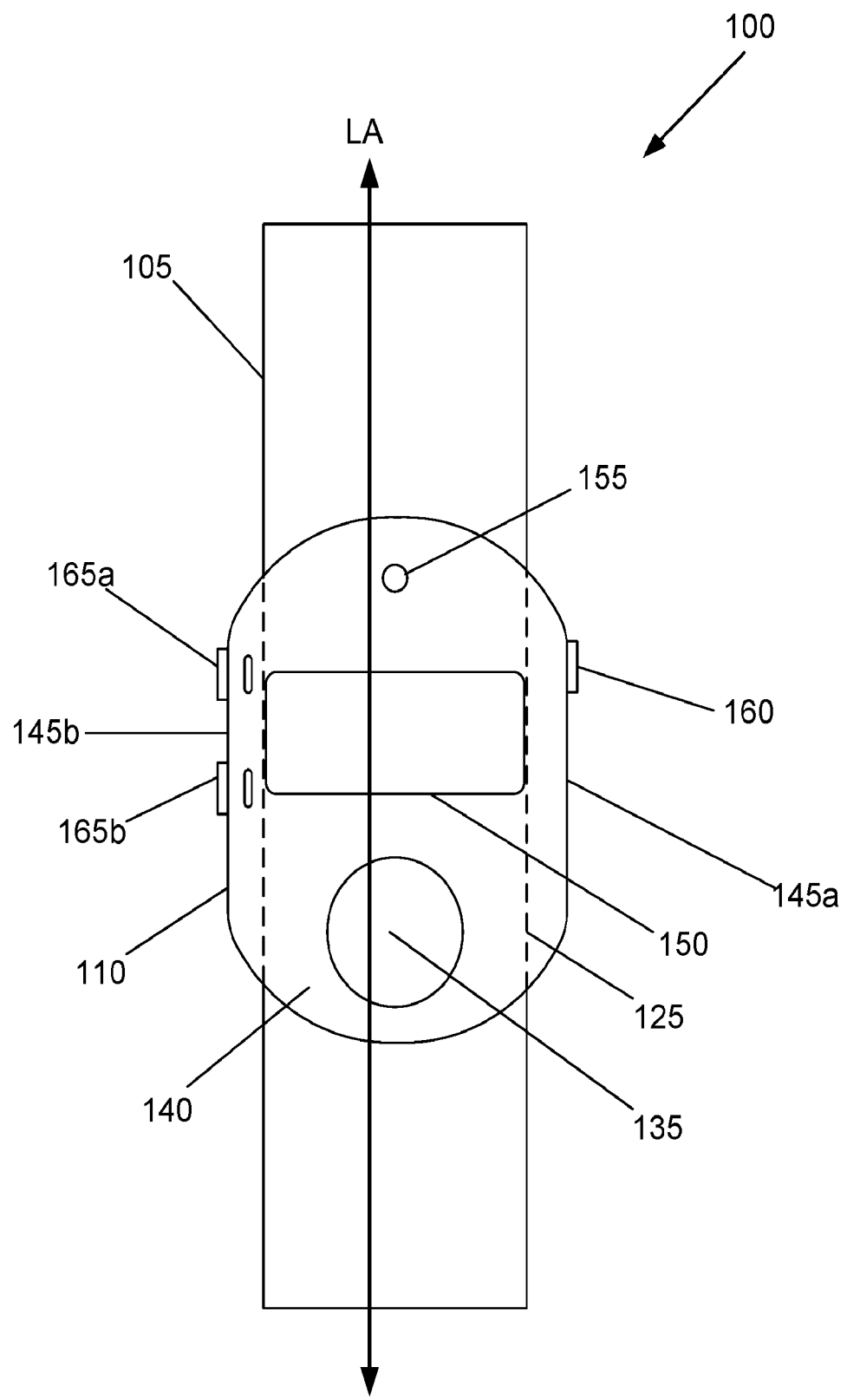
FIG. 2 is a front view of the smart tourniquet.

FIG. 2 shows an example of the recording module 110 having a face 140, and opposing first side 145a and second side 145b that are aligned with the long dimension of the recording module 110. The face 140 includes a display 150 for showing the patient for information, e.g., a timestamp of an infusion. The display 150 can be an LCD (liquid crystal display) panel. As shown, on the face 140 near the display 150 there is an indicator 155 for providing visual cues to the patient. The indicator 155 can be an LED (light-emitting diode) light that is illuminated when the smart tourniquet 100 is "awake" and ready to record a timestamp. The LED light is not illuminated when the smart tourniquet 100 is "asleep" and not ready to record a timestamp. Beneficially, the patient can readily tell whether the smart tourniquet 100 is ready for them to use by looking at the indicator 155. As another example of information conveyed by the indicator 155, a blinking LED can indicate that the smart tourniquet 100 is not functioning properly and requires servicing or replacement.

In the arrangement shown in FIG. 2, along the first side 145a of the recording module 110, there is a function key 160 for switching operating modes of the smart tourniquet 100, as will be described later in greater detail. Additionally, along the second side 145b of the recording module 110, there is a first key 165a and a second key 165b for inputting information into the recording module 110. The first key 165a and the second key 165b can be used to increase or decrease the value of an input. The first key 165a and the second key 165b can also be used to go forward or backward when selecting an input to enter. For ease of reference, the first key 165a and the second key 165b are called a "plus key" and a "minus key", respectively; and collectively "plus/minus keys" 165. Independent of their label, the plus/minus keys 165 are used to enter information, as will be described in greater detail below.

The keys can be in the form of a button or a bar, just to name a few possible shapes. For example, the plus/minus keys 165 can be a "toggle" bar that acts as a plus button or minus button depending upon which end of the toggle bar the patient presses. The keys can also be multifunctional. In a convenient example, the function key 160 can have the added function of recording a timestamp. In this example, the patient holds down the function key 160 for a predetermined period of time (e.g., at least three seconds) to record a timestamp. Advantageously, the foregoing example provides an alternative way of recording a timestamp adding robustness and increasing usability of the smart tourniquet 100.

One or more keys can be used to turn on and/or off the smart tourniquet 100. For example, pressing and holding the plus/minus keys 165 for three second turns on the smart tourniquet 100. Doing the same again turns the smart tourniquet 100 off. It should be appreciated that the smart tourniquet 100 can be designed to turn on and/or off using any combination on keys and hold down times.

In an alternative example, there are no keys and the display 150 is sensitive to the patient's touch. In this "touchscreen" example, physical keys are replaced with icons shown on the display 150 that the patient can touch. Any of the aforementioned functions can be accessed by the patient with one or more taps of the touchscreen.

As described above, the smart tourniquet 100 can record the dosage or "number of units" of medication taken by the patient and recall records of past infusions. These and other features are described with reference to FIGS. 3-5 with additional reference to FIG. 2. Starting with FIG. 3 the figure shows a series of interfaces 200 for activating the operating modes of the smart tourniquet 100. The series 200 includes a welcome interface 205, a dosage input interface 210, a record inquiry interface 215, a time adjustment interface 220, and language interface 225. These interfaces can be shown on the display 150 as screens. The welcome interface 205 or "home screen" can provide information such as the current date and time. Other information that can be provided to the patient, include instructions on how to use the smart tourniquet 100, a firmware version number, and legal information.

Figure 3:
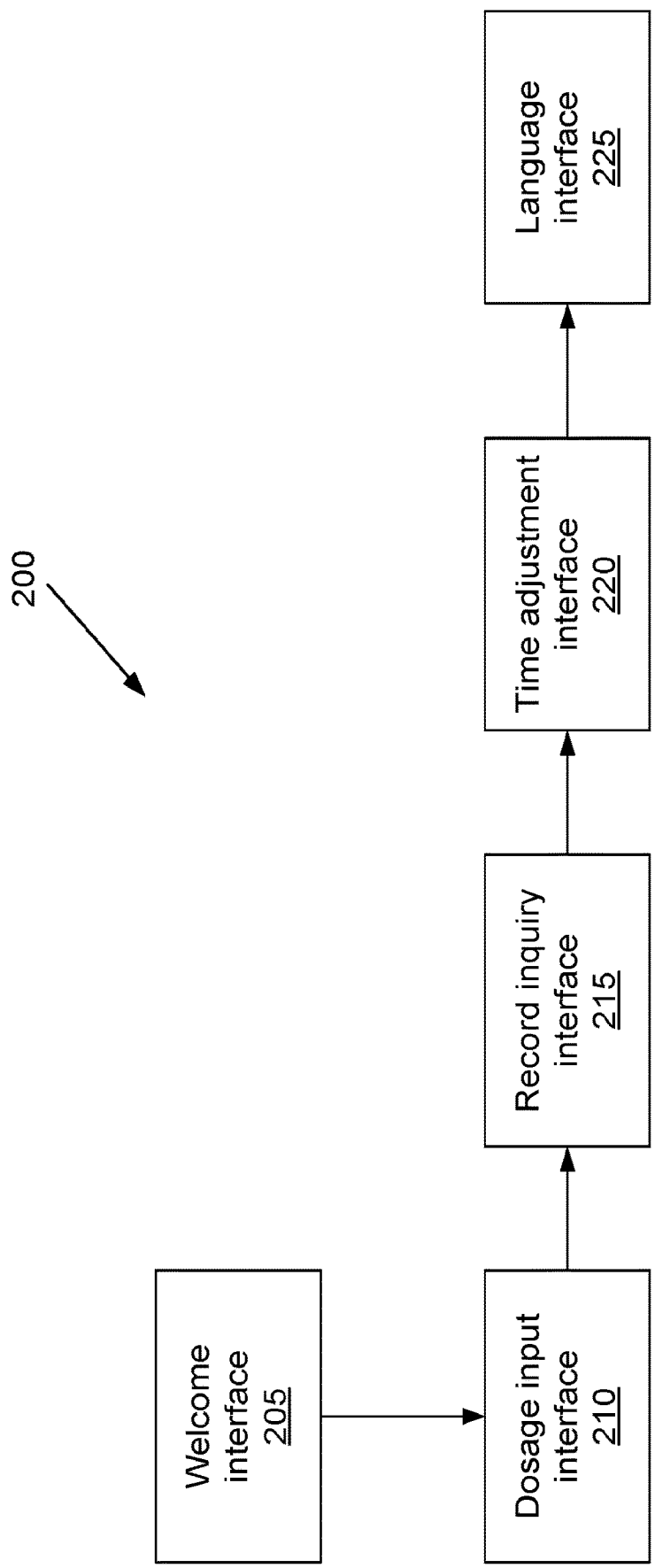
FIG. 3 is an organizational diagram of smart tourniquet operating modes.
Figure 4A:
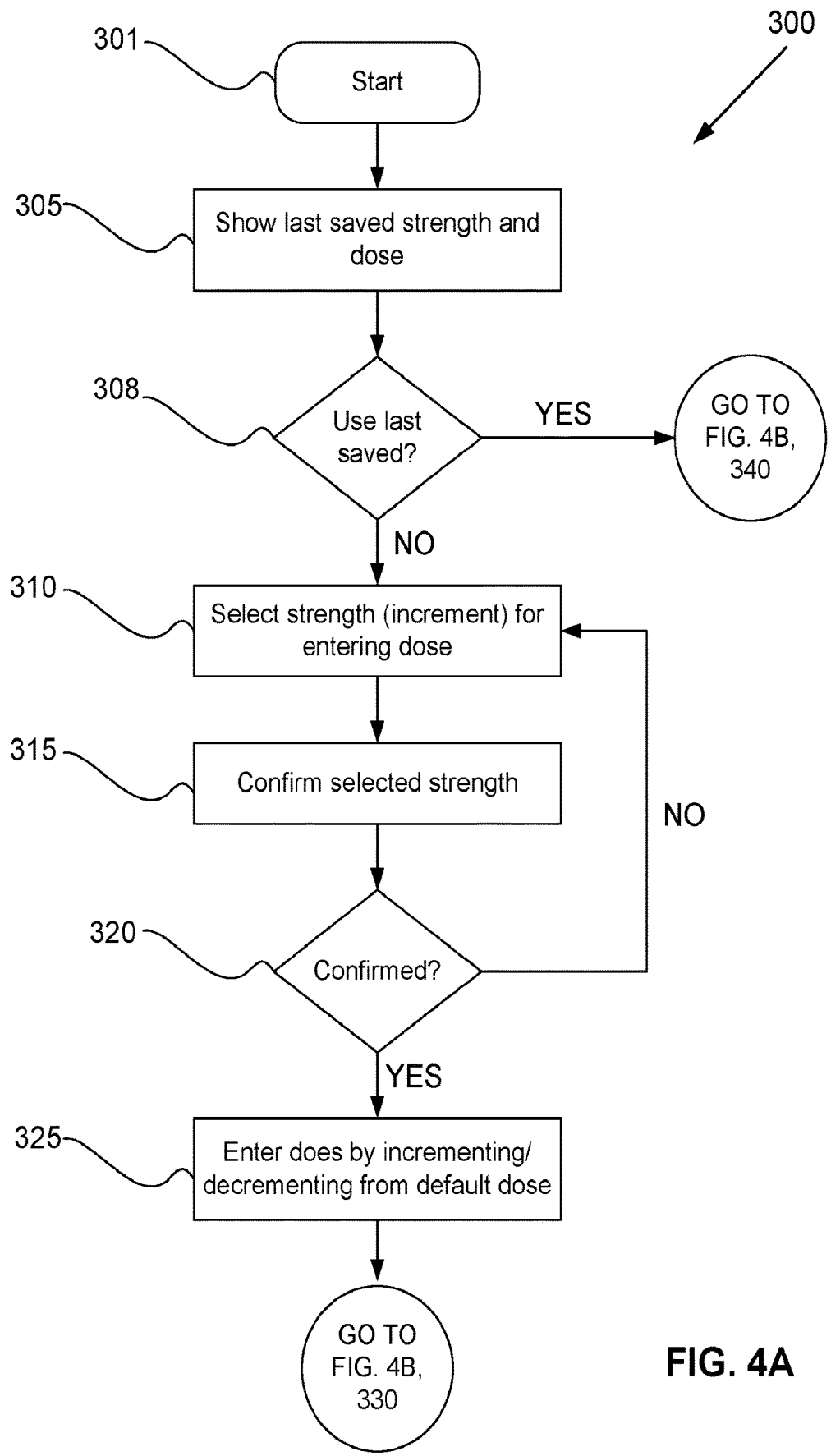
FIGS. 4A-B is a flow chart for operating the smart tourniquet in a dosage inputting mode.

The patient switches between the interfaces to select an operating mode. By way of non-limiting example, the smart tourniquet 100 starts (e.g., after the smart tourniquet 100 wakes up) with the welcome interface 205. The patient can press the function key 160 on the recording module 110 to switch from the welcome interface 205 to the dosage input interface 210. At this time, the patient can wait for the dosage input operating mode to activate or the patient can press the function key 160 again to switch to the next interface, the record inquiry interface 215. The user can cycle through the series of interfaces 200, again and again, until an operating mode is activated. There can more or fewer interfaces as shown in FIG. 3 so long as the patient can activate an operating mode.

For a more complete record of an infusion, the dosage of medication that was taken can be tracked along with the date and time of an infusion. Knowing when and how much medication can be helpful to devising a dosing plan, for example. By convention, a medication dosage is measured in International Units (IU's). FIG. 4 shows an example of the smart tourniquet 100 functioning in the dosage input operating mode, referred to as process 300 for ease of reference. Interactions between the process 300 and the patient can be carried out using the function key 160, the plus/minus keys 165, and the display 150, as described above.

The process 300 starts (301) with the patient switching to the dosage input interface 210 and activating the dosage input operating mode, as described above with reference to FIG. 3. The process 300 shows the patient the strength and dosage saved from the last infusion and asks (308) whether they want to use the saved values. When the process 300 receives a "yes" from the patient, the process 300 jumps forward to step 340 of FIG. 4B and asks the patient to confirm recording the strength and dosage from the last infusion. Advantageously, this saves the patient time by not having them reenter information when there is no change from the prior infusion.

Returning to FIG. 4A, when the process 300 at check 308 receives a "no" from the patient, the process 300 then asks (310) the patient to select a strength (increment) for entering the dosage. The patient uses the plus/minus keys 165 to make the strength selection. As a non-limiting example, the patient pushes the minus key 165b to select the strength of 250 IU and pushes the plus key 165a to select the strength of 500 IU.

The process 300 asks (315) the patient to confirm the strength selected. The patient uses the plus/minus keys 165 to confirm the strength selection (e.g., the patient pushes the minus key 165b for no and pushes the plus key 165a for yes). When the process 300 at check 320 receives a "no" from the patient; the process 300 returns to asking (310) the patient to select the strength. When the process 300 at check 320 receives a "yes" from the patient, the process 300 provides (325) a default dosage. The default dosage can be the last dosage entered by the patient.

The patient uses the plus/minus keys 165 to increase or decrease the default dosage by the selected strength. As a non-limiting example, the patient selects and confirms the strength of 250 IU. The patient pushes the plus key 165a to increase the default dosage of 1000 IU by 250 IU, resulting in a dosage of 1250 IU being entered. The patient pushes the minus key 165b to decrease the default dosage of 1000 IU by 250 IU, resulting in a dosage of 750 IU being entered.

Figure 4B:
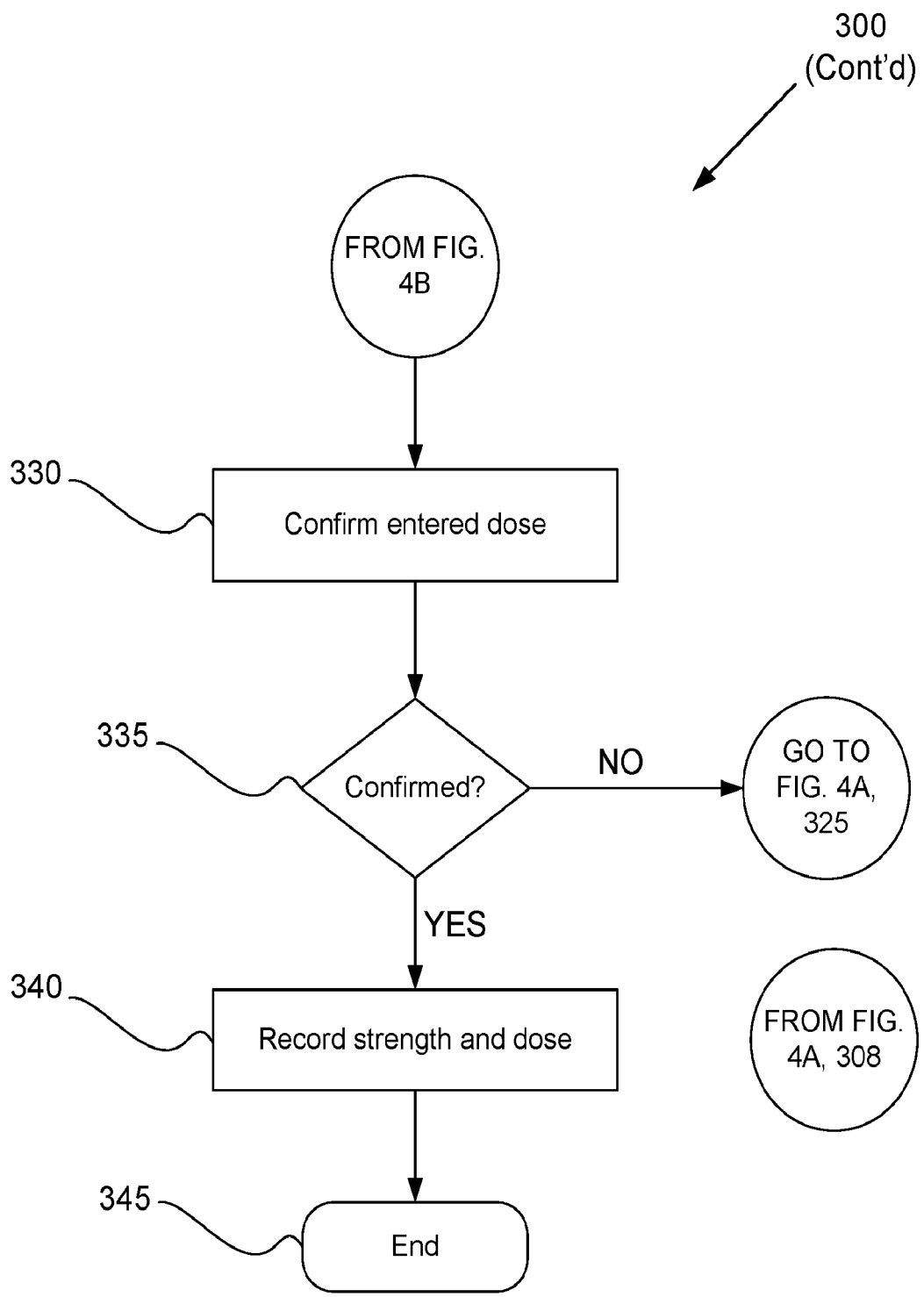

Continuing with FIG. 4B, after the patient enters the dosage, the process 300 asks (330) the patient to confirm the entered dosage. The user uses the plus/minus keys 165 to confirm the dosage entry (e.g., the patient pushes the minus key 165b for no and pushes the plus key 165a for yes). When process 300 at check 335 receives a "no" from the patient; the process 300 returns to providing (325 of FIG. 4A) the default dosage to the patient to increase or decrease by the selected strength. When the process 300 at check 335 receives a "yes" from the patient, the process 300 records (340) the entered dosage. The process 300 ends (345) with the patient being returned to the dosage input interface 210. The patient can also be brought to the welcome interface 205.

In a convenient example, the process 300 records the entered dosage such that data representing dosage and timestamp of an infusion are associated or otherwise linked together. Advantageously, a dosage can be looked by based on a timestamp. Alternatively, a dosage can used to look up one or more timestamps. Such information can be useful in analyzing how well the patient is responding to the infusions, for example.

Figure 5:
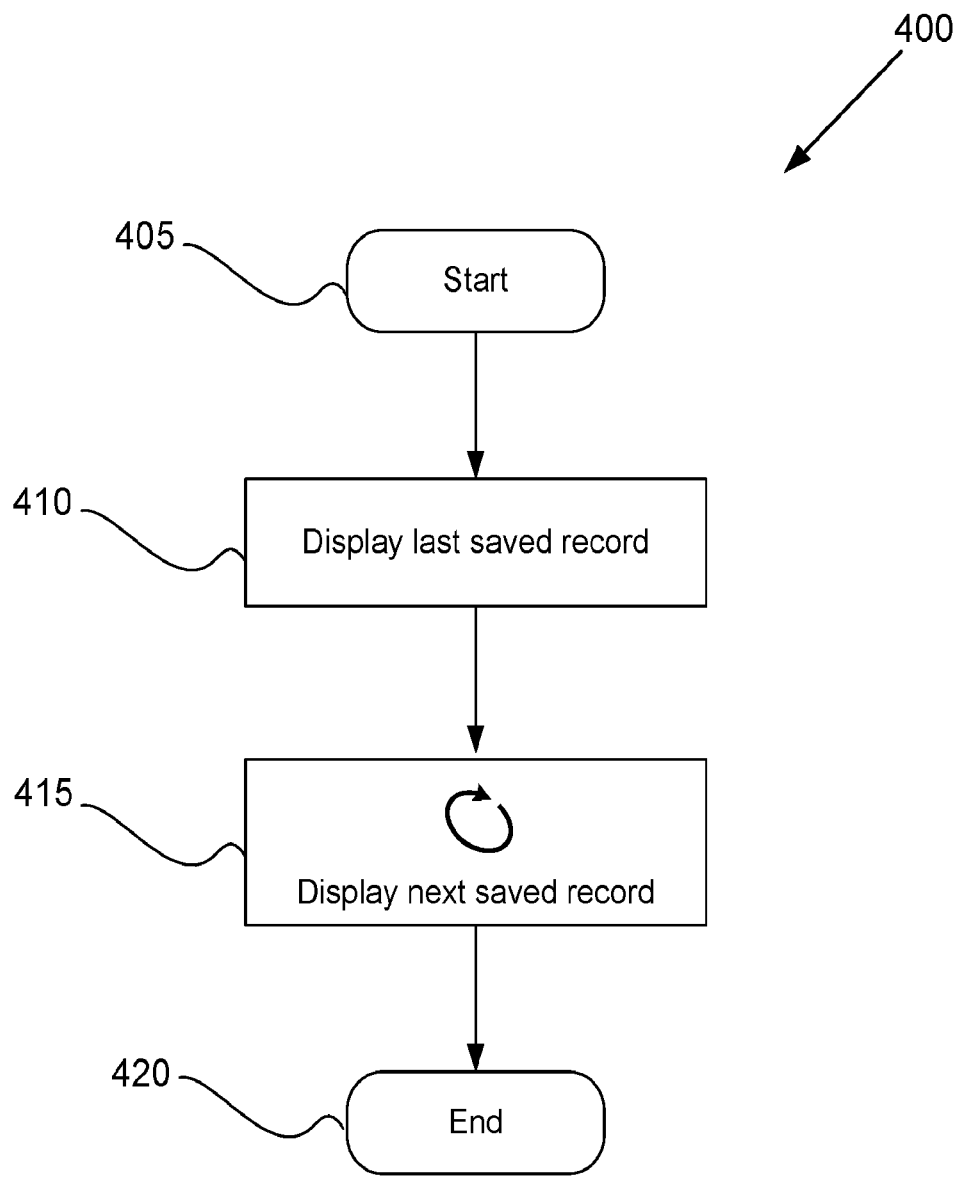
FIG. 5 is a flow chart for operating the smart tourniquet in a record inquiry mode.

It may be helpful to know when in the past, the patient has taken medication and, in some instances, how much they took. For example, a doctor can review a history of past infusions to analyze the effectiveness of a prescribed treatment. As another example, the patient can use the date and time of their last infusion to determine whether it is time for their next infusion. FIG. 5 shows an example of the smart tourniquet 100 functioning in the record inquiry operating mode, which for ease of reference is referred to as process 400. The process 400 provides the patient with the ability to recall timestamps of past infusions or "records." A record can also include the medication dosage taken at the time of the infusion. Interactions between the process 400 and the patient can be carried out using the function key 160, the plus/minus keys 165, and the display 150, as described above.

The process 400 starts (405) with the patient switching to the record inquiry interface 215 and activating the record inquiry operating mode, as described above with reference to FIG. 3. The process 400 shows (410) the last saved record on the display 150, including the timestamp of the last infusion. The patient can use the plus/minus keys 165 to see the "next saved record." The records can be organized in reverse chronological order, with the newest record shown first and the oldest record shown last. In response to the patient pressing the plus/minus keys 165, the process 400 displays (415) the next saved record. As the patient continues to press the plus/minus keys 165, the process 400 continues to display (415) the next saved record (which is represented in the figure as a looped arrow). The process 400 can stop displaying (415) the next saved record when all the saved records have been shown to the patient. Alternatively, the process 400 can continue displaying (415) the next saved record, looping through the saved records, as long as the patient continues to press the plus/minus keys 165. The process 400 ends (420) when the patient presses the function key 160 to exit the record inquiry operating mode and returned to the welcome interface 205.

As described earlier, the recording module 110 can include a clock for providing date and time of an infusion. The clock could be set manually, for example, the patient can use the function key 160 and the plus/minus keys 165 to set the date and time. The clock can also be set automatically without the patient's intervention. For example, the smart tourniquet 100 can be synchronized with an application and the clock can be set by the application. In this example, the patient switches to the time adjusting interface 220 to activate the time adjusting operating mode. The smart tourniquet 100 acquires the present date and time from the application (e.g., by querying the application) to adjust the clock. (The synchronization process between the smart tourniquet 100 and the application will be described in greater detail below.) In another example, the smart tourniquet 100 can be connected to the Internet and receive date and time information according to a networking protocol for clock synchronization, such as the Network Time Protocol (NTP). In yet another example, the smart tourniquet 100 can receive wireless signals carrying date and time information, such as a beacon frame transmitted by a WIFI access point.

Synchronizing the smart tourniquet 100 with an application can be useful because the patient's infusion records can be sent from the smart tourniquet 100 to the application. The application can then, for example, combine the records with other information (which may have been given by the patient using the application) and provide analytics, which can help the patient manage their own care. For a hemophilia sufferer, who is taking an infusion of recombinant Factor VIII, the information entered into the application can include the reason for the infusion (e.g., prophylaxis, spontaneous, injury, surgery/dental, follow-up or other). Such information can also be made available to a network of care providers to provide the patient with more complete care.

Figure 6:
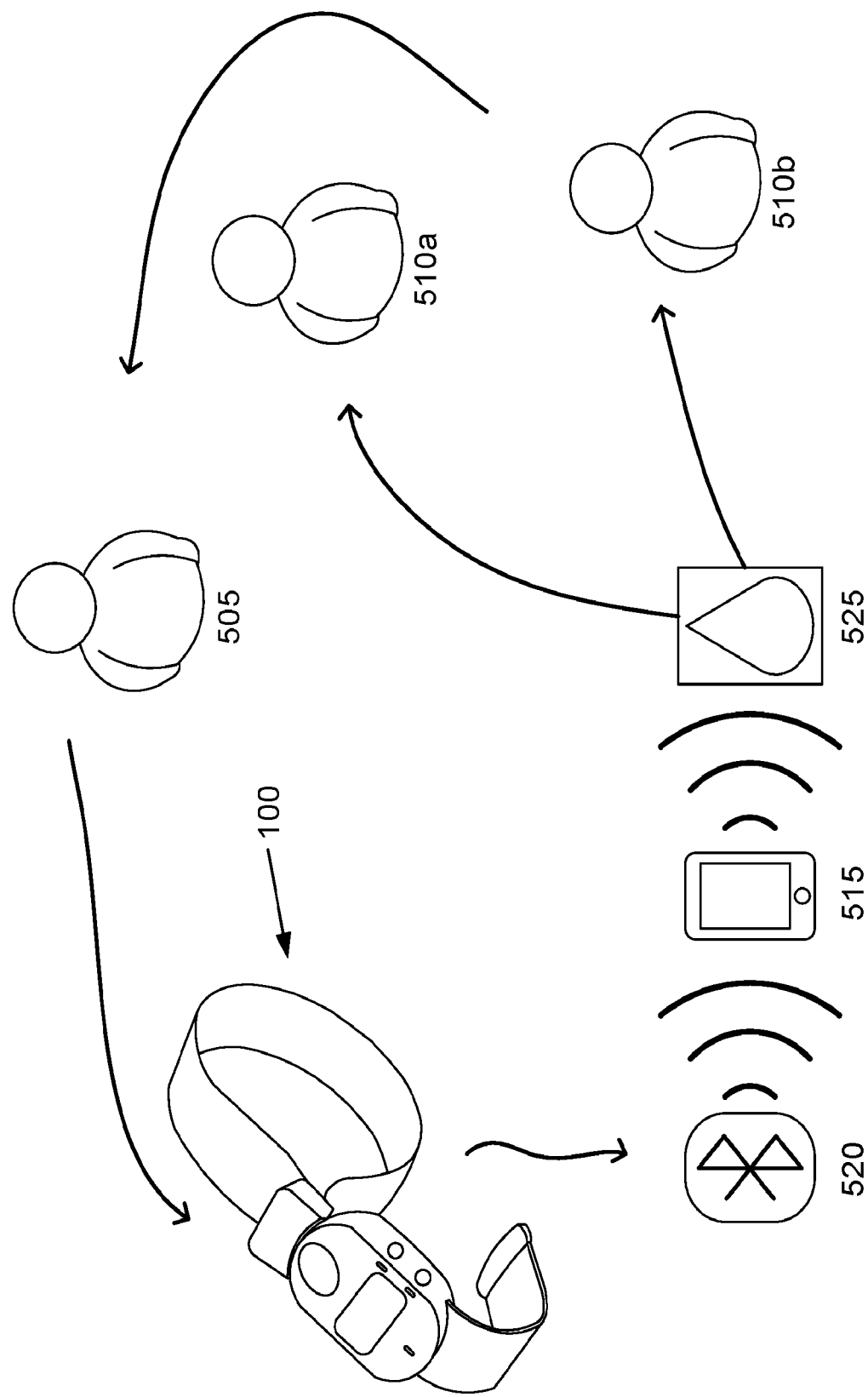
FIG. 6 is a diagram of an example care network.

FIG. 6 shows an example care network 500, including a patient 505, and healthcare providers, such as doctor 510a and nurse 510b, collectively referred to as 510. The patient 505 uses the smart tourniquet 100 for self-administer infusions and to record the date and time of the infusions, as described above. The smart tourniquet 100 is wirelessly connected to a computing device 515 in accordance with any number of wireless communication protocols, such as BLUETOOTH, WIFI, ZIGBEE, and ZWAVE just to name a few.

The smart tourniquet 100 is wirelessly connected to a computing device 515 using a wireless communication protocol 520. As shown in the example, the wireless communication protocol 520 is BLUETOOTH. The wireless communication protocol 520 can also be WIFI, ZIGBEE, and ZWAVE just to name a few. The computing device 515 can be a smartphone or other mobile device (as shown), and can run an application 525 that is a companion to the smart tourniquet 100. When connected to the computing device 515, the smart tourniquet 100 can be synchronized with the application 525, and records and other information can be sent to the computing device 515. Downloading the records to the computing device 515 is advantageous because there is more memory to store the records than on the smart tourniquet 100. Additionally, the computing device 515 has more computing power to perform analytics.

Another benefit to transferring saved records from the smart tourniquet 100 is that the records can then be shared with the healthcare providers 510, along with other patient information. The computing device 515 is coupled to a network, such as the Internet or a private network (not shown). The healthcare providers 510 can access the patient's information, including records of self-administered infusions, by sending and receiving electronic messages (e.g., requests and responses) over the network. The electronic messages can be secured to provide privacy and security of health information in accordance with local regulations (e.g., in the U.S., the Health Insurance Portability and Accountability Act or "HIPAA").

Based on the information provided by the patient using the smart tourniquet 100 and application, the healthcare providers 510 can analyze the effectiveness of the prescribed treatment and, in some instance, modify that treatment. Advantageously, the care network 500 includes the patient 505 and their feedback in rendering them care.

The care network 500 is advantageous because it connects the patient 505 with the healthcare providers 510. Additionally, the care network 500 enables information about infusions to be automatically collected (by way of the smart tourniquet 100), thereby reducing any delay in delivering that information to the healthcare providers 510. For example, infusion information is collected in response to the smart tourniquet 100 being synchronized with the application 525. In turn, the healthcare providers 510 can provide the patient 505 with care that is timely and accurate.

Figure 7B:
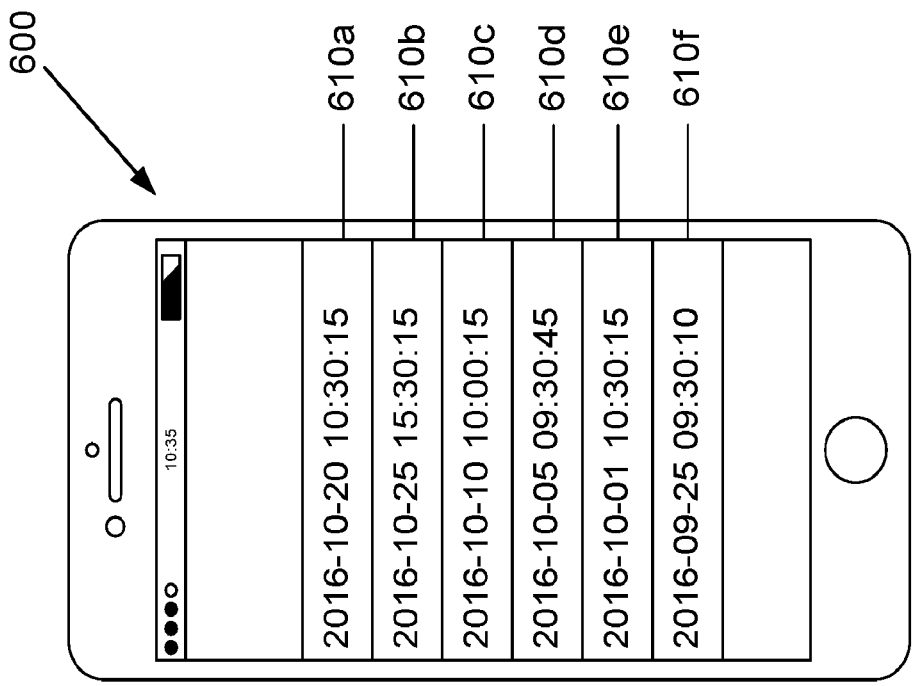
FIGS. 7A-7D is a series of screenshots of an example application for synchronizing with the smart tourniquet.
Figure 7A:
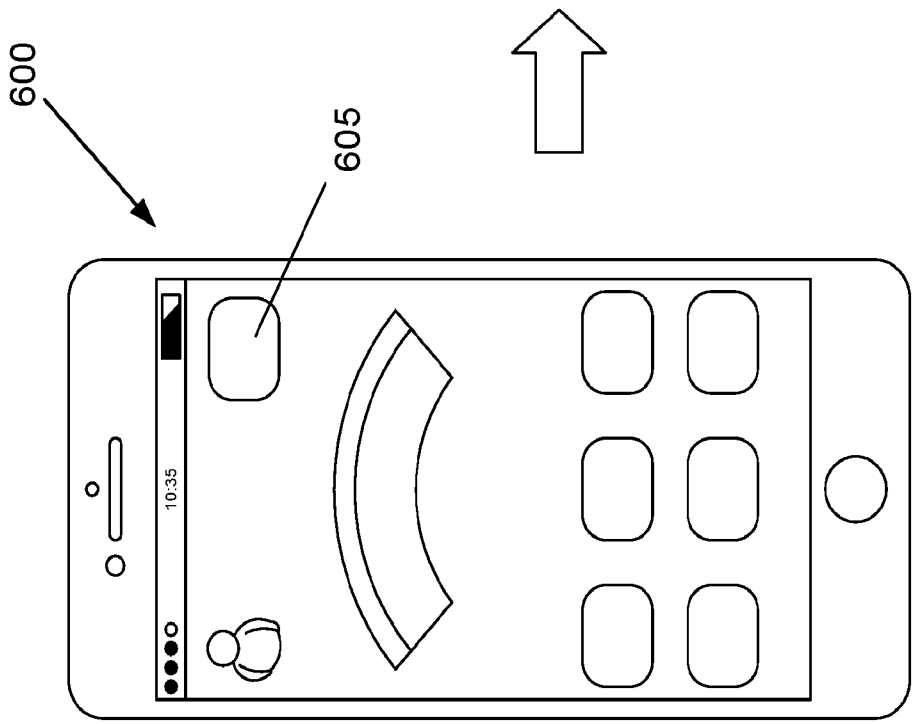
Figure 7D:
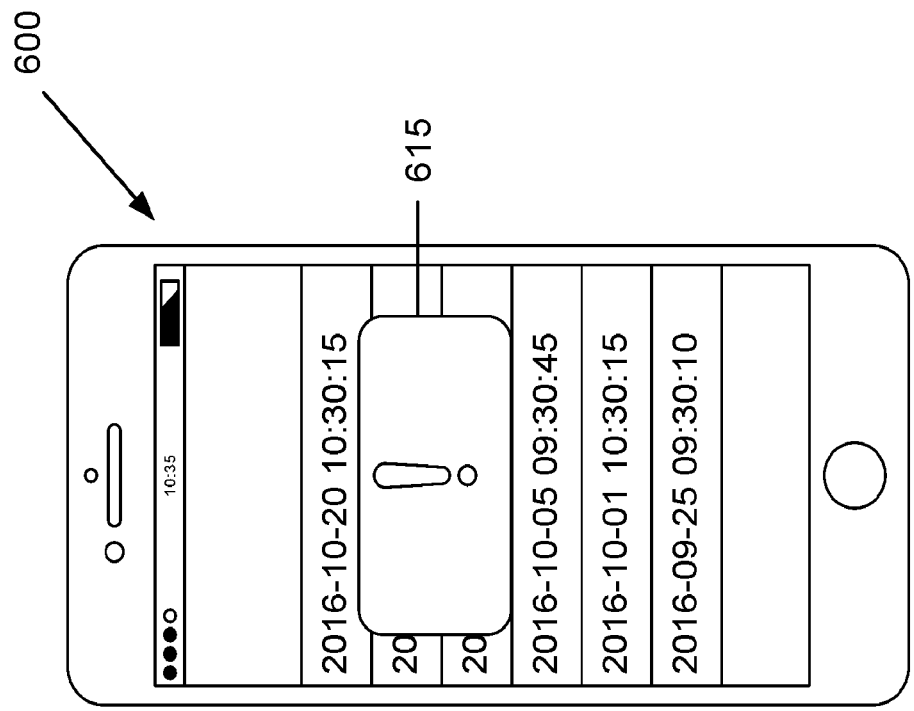
Figure 7C:
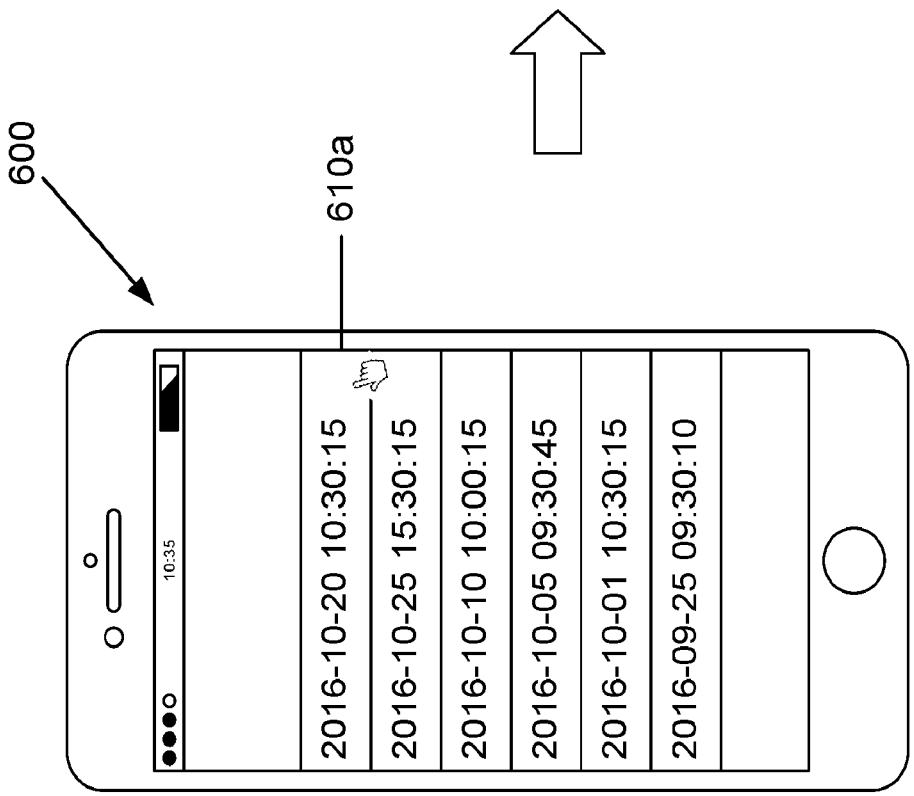

FIGS. 7A through 7D show a series of screenshots of an application 600 used by a hemophilia sufferer to track infusions of recombinant Factor VIII. As shown in FIG. 7A, the application 600 includes a virtual button 605 that the person presses to synchronize and download records of past infusions from a smart tourniquet (such as the smart tourniquet 100 of FIGS. 1 and 2). In FIG. 7B, the application 600 can display downloaded records 610a-f as a list. In FIG. 7C, the person selects the record 610a (shown in the figure as a pointing icon). In FIG. 7D, in response to the selection, the application 600 provides a popup window 615 asking the person to identify the reason for the selected infusion as being either preventative (e.g., prophylactic treatment) or treatment (e.g., to stop spontaneous bleeding). Advantageously, the application 600 guides the person through the steps for providing more information about infusions, the timestamps of which were recorded by the smart tourniquet without the patient having to enter in the timestamps.

Example uses of a smart tourniquet, such as the smart tourniquet 100 of FIGS. 1 and 2, are described with reference to the remaining figures in this disclosure. The uses are described in terms of the actions taken by the patient (which are identified in the figures by the label "Operation:") and information displayed and recorded by the smart tourniquet (which are identified in the figures by the labels "Display:" and "Record:"). In some instances, the smart tourniquet could does not record information and this is denoted in the figures as "NA" for not applicable.

For the sake of discussion, the records are described as being saved to a "database". The database is shown in the figures as a table having rows and columns. Each row of information represents a collection of related information. Those skilled in the art will readily recognize that the records can be implemented as any number of data structures, such as a linked list or an array.

FIGS. 8, 9A-B, and 10A-C show the patient using the smart tourniquet to take an infusion, including waking up the smart tourniquet, and inputting the strength and dosage taken. In FIG. 8, the patient wakes up the smart tourniquet by tightening the device around their arm. In response, the smart tourniquet saves a first record (labeled in the figure as "SN 1") that includes the date and time when the device woke up (i.e., a wakeup timestamp). Because the patient does not take an infusion at the same time as the device wakes up, strength and dosage values associated with the wakeup time is are "NULL" as shown in the figure.

FIGS. 9A-B show the patient using the smart tourniquet to input the strength and dosage of the infusion they took. In FIG. 9A, the patient switches to a 'Dosage' screen (e.g., the dosage input interface 210 of FIG. 3) and activates the dosage input operating mode, as described above with reference to FIG. 3. In FIG. 9B, the smart tourniquet displays the last saved strength and dosage. In the event there is no last saved strength and dosage (e.g., the smart tourniquet is being used for the first time or after being reset), the device displays a value of zero. In the example shown, the strength and dosage of the infusion is the same as the last saved strength and dosage. The patient confirms the last saved strength and dosage. In response to the confirmation, the smart tourniquet saves a second record (labeled in the figure as "SN 2") that includes the date and time of when the strength and dosage are confirmed (i.e., a confirmation timestamp). In a convenient example, the smart tourniquet displays 'Success' for 3 second (or other amount time) and returns to 'Dosage' screen.

FIGS. 10A-C show the smart tourniquet in the dosage input operating mode and patient entering the strength and dosage of an infusion that is different than a prior infusion. In FIG. 10A, the patient selects the strength and then in FIG. 10B, adjusts a dosage by incrementing (as is shown) or decrementing by that strength until the desired dosage is reached. In FIG. 10C, the patient confirms the inputted dosage. The smart tourniquet, in turn, saves a third record (labeled in the figure as "SN 3") that includes the date and time of when the strength and dosage are confirmed. In a convenient example, the smart tourniquet does not add a record with zero dosage to the database (i.e., a confirmation timestamp). The smart tourniquet displays 'Success' for 3 seconds (or other amount time) and returns to 'Dosage' screen.

FIGS. 11A-D show the patient using the smart tourniquet to review infusion records stored in the device. In FIG. 11A, the patient switches to a 'Records' screen (e.g., the record inquiry interface 215 of FIG. 3) and activates the record inquiry operating mode, as described above with reference to FIG. 3. In FIG. 11B, the smart tourniquet displays the last saved record that includes the timestamp, strength, and dosage of the last infusion. In FIG. 11C, the patient can view other infusion records using, for example, the plus/minus keys 165 of FIGS. 1 and 2. The smart displays records having strength and dosage values that are not NULL. This feature can help a patient differentiate between times when they actually took an infusion from times when they started to but for some reason did not take an infusion. This is particularly beneficial considering patients typically have full and active lives making it difficult from them to recall past events clearly. In FIG. 11D, the patient presses the function button to return to the 'Records' screen.

FIGS. 12A-C show the patient adjusting the time on the smart tourniquet. In FIG. 11A, the patient switches to a 'Time Adjustment' screen (e.g., the time adjustment interface 220 of FIG. 3) and activates the time adjustment operating mode, as described above with reference to FIG. 3. In FIGS. 12B-C, while in this mode, the patient can adjust the time as shown. In FIG. 12D, the patient presses the function button to return to the 'Time Adjustment' screen.

FIGS. 13A-D show the patient selecting which language the smart tourniquet communicates with the patient. In FIG. 13A, the patient switches to a 'Language' screen (e.g., the language interface 225 of FIG. 3) and activates a time adjustment operating mode. In the example shown, the 'Language' screen is written in Chinese. In FIGS. 13B-C, while operating in this mode, the patient can select a language from the languages available on the smart tourniquet. In the example shown, the patient selects English. In FIG. 13D, the patient presses the function button to return to the 'Language' screen, which is now written in English.

As described previously, the smart tourniquet can be synchronized with an application, such as the application 525 of FIG. 6. Once synchronized, infusions records can be transferred to the application for analysis and/or sharing with others. The synchronization process can include establishing a connection (e.g., a wireless BLUETOOTH connection) between the smart tourniquet and the application. FIG. 14 shows the patient confirming that a connection between the smart tourniquet and the application be established. (In the example shown, the application is running on a mobile phone and the connection is being made between the smart tourniquet and the mobile phone.) In a convenient example, the patient is asked to confirm the connection in response to the smart tourniquet receiving a request from the application to connect.

As described above, the smart tourniquet 100 can help the patient record when they took an infusion of a drug. It should be noted that the usefulness of the smart tourniquet 100 extends beyond a single particular drug but can be readily applied to any drug administered, intravenously, made by any pharmaceutical company. It is common practice in the drug industry for a drug marker to design and market a drug delivery device, such as an auto injector, that must be used to administer their drug. For example, a patient can only inject themselves with company X's insulin using company X's insulin pen (even if company Y's device is easier for patient to use). Advantageously, the smart tourniquet 100 is not tied to a particular drug and can be widely adopted by pharmaceutical companies and patients alike.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

Any and all references and citations to other documents, such as patents, patent applications, patent publications, journals, books, papers, and web contents, which have been made throughout this disclosure, are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:
1. A tourniquet for self-administrating a drug, the tourniquet comprising:
    an elongate member including a first end and a second end, and a longitudinal axis extending between the first end and the second end, the elongate member being adapted for wrapping about a limb of a patient;
    a recording module including: a) a slot extending therethrough for slidably receiving the elongate member and b) an fastening end for releasably capturing the second end of the elongate member; and an electrode electrically coupled to the recording module that contacts the patient's skin when the tourniquet is tightened about the limb of the patient; and when the elongate member is wrapped about the limb of the patient and the second end of elongate member is captured by the fastening end so that the second end is fixed to the recording module, in response to pulling the first end of the elongate member away from the second end in the longitudinal direction: a) the tourniquet tightens about the limb and b) the recording module saves in a record, a timestamp of the patient using the tourniquet to self-administer a drug, wherein the recording module is configured to save the timestamp in response to a galvanic skin response measured by the electrode.

2. The tourniquet of claim 1, wherein the recording module saves a confirmation timestamp in response to the patient confirming a strength and dosage of the drug.

3. The tourniquet of claim 1, wherein the second end of the elongate member and fastening end of the recording module form a buckle assembly comprising a male portion and a female portion.

4. The tourniquet of claim 1, wherein the recording module includes a wireless interface for communicating with a computing device.

5. The tourniquet of claim 4, wherein the wireless interface communicates with the computing device using any one of BLUETOOTH, WIFI, ZIGBEE, and ZWAVE.

6. The tourniquet of claim 1, wherein the recording module includes a display and one or more keys for: i) entering the dosage of the drug self-administered by the patient so that the record includes the timestamp and the dosage, ii) inquiring about past records, iii) adjusting the timestamp, iv) changing the language of text displayed by the recording module or v) a combination thereof.

7. The tourniquet of claim 1, wherein the recording module includes a function key, which when depressed and held for at least a pre-defined period of time causes the recording module to save the timestamp of the patient using the tourniquet to self-administer the drug.

8. The tourniquet of claim 1, wherein the recording module includes memory for storing the record and previous records with earlier timestamps of the patient using the tourniquet to self-administer the drug.

9. The tourniquet of claim 1, wherein the recording module includes an audio alarm configured to provide an aural cue in response to the fastening end of the recording module capturing the second end of the elongate member.

10. The tourniquet of claim 1, wherein the recording module includes a visual alarm configured to provide a visual cue in response to the fastening end of the recording module capturing the second end of the elongate member.

11. The tourniquet of claim 1, wherein the recording module shuts off in response to the second end being released from the fastening end.

12. A method for tracking when a patient self-administers a drug, the method comprising:

providing a tourniquet comprising:
an elongate member including a first end and a second end, and a longitudinal axis extending between the first end and the second end, the elongate member being adapted for wrapping about a limb of a patient;

a recording module including: a) a slot extending therethrough for slidably receiving the elongate member and b) an fastening end for releasably capturing the second end of the elongate member; and an electrode electrically coupled to the recording module;

saving in the recording module a record including a timestamp of the patient using the tourniquet to self-administer a drug; and wherein the saving is in response to the second end of elongate member being captured by the fastening end of the recording module and the tourniquet being tightened about the limb such that the electrode detects a galvanic skin response.

13. A tourniquet for self-administrating a drug, the tourniquet comprising:

an elongate member including a first end and a second end, and a longitudinal axis extending between the first end and the second end, the elongate member being adapted for wrapping about a limb of a patient;

a recording module including: a) a slot extending therethrough for slidably receiving the elongate member and b) an fastening end for releasably capturing the second end of the elongate member; and when the elongate member is wrapped about the limb of the patient and the second end of elongate member is captured by the fastening end so that the second end is fixed to the recording module, in response to pulling the first end of the elongate member away from the second end in the longitudinal direction: a) the tourniquet tightens about the limb and b) the recording module saves in a record, a record timestamp of the patient using the tourniquet to self-administer a drug, wherein the recording module saves a confirmation timestamp in response to the patient confirming a strength and dosage of the drug.

14. The tourniquet of claim 13 further comprising an electrode electrically coupled to the recording module that contacts the patient's skin when the tourniquet is tightened about the patient's limb; and wherein the recording module is configured to save the record timestamp in response to a galvanic skin response measured by the electrode.

15. The tourniquet of claim 13, wherein the recording module includes a function key, which when depressed and held for at least a pre-defined period of time causes the recording module to save the record timestamp of the patient using the tourniquet to self-administer the drug.

16. The tourniquet of claim 13, wherein the recording module includes memory for storing the record and previous records with earlier record timestamps of the patient using the tourniquet to self-administer the drug.

17. The tourniquet of claim 13, wherein the recording module includes an audio alarm configured to provide an aural cue in response to the fastening end of the recording module capturing the second end of the elongate member.

18. The tourniquet of claim 13, wherein the recording module includes a visual alarm configured to provide a visual cue in response to the fastening end of the recording module capturing the second end of the elongate member.

19. The tourniquet of claim 13, wherein the recording module shuts off in response to the second end being released from the fastening end.

* * * * *